United States Patent [19]

Conn

[11] Patent Number: 4,618,598

[45] Date of Patent: Oct. 21, 1986

[54] METHOD OF REGULATING HORMONE FUNCTION OR RELEASE

[75] Inventor: P. Michael Conn, Durham, N.C.

[73] Assignee: Duke University, N.C.

[21] Appl. No.: 367,339

[22] Filed: Apr. 12, 1982

[51] Int. Cl.[4] .......................... A61K 37/00; A23J 7/00; C07K 1/00; G01N 53/00

[52] U.S. Cl. ........................................... 514/6; 514/2; 514/12; 514/13; 514/874; 435/7; 530/313; 530/399

[58] Field of Search ................. 424/177, 108, 109, 94, 424/85; 260/112.5, 112 R; 435/7; 514/2, 6, 12, 13

[56] References Cited

PUBLICATIONS

Conn et al., *Endocrinology*, 1979, vol. 105, pp. 1122–1127, "Alteration of the Intracellular . . . Rat Anterior Pitu. Cells".
Conn et al., *Endocrinology*, 1980, vol. 107, pp. 2133–2134, "Gonadotropin Release from Pituitary Culture".
Conn et al., *J. Biol. Chem* (Feb. 10, 1981) pp. 1098–1100, "Stimulation of Pituitary Gonodotropin Release".
Conn et al., (including Deloris C. Rogers, M. Stewart, James Niedel, and Timothy Sheffeld) *Nature*, Apr. 15, 1982, pp. 653–655.
The Merck Index, 9th Edition, pp. 425, 298, 848, 1002, and 1277.

*Primary Examiner*—Thomas G. Wiseman
*Assistant Examiner*—Robin Lyn Teskin
*Attorney, Agent, or Firm*—Oblon, Fisher, Spivak, McClelland & Maier

[57] ABSTRACT

A synthetic hormone complex comprising means for binding to the surface of a cell and means for altering second messenger mobilization by the cell. One form of the synthetic hormone complex functions as an antagonist with specific binding affinity for a cell receptor, said hormone in combination with a calcium ion channel inhibitor. Another synthetic hormone complex functioning as an Agonist comprising two or more molecules of a hormone having specific binding affinity for a cell receptor wherein a spacer binding the hormones is 10 to 300 angstroms in length. A method of regulating hormones or other regulatory factors comprising contacting a synthetic hormone complex with a cell surface or internal receptor thereby altering the incorporation of second messenger molecules thereby regulating the physiological function of the cell.

26 Claims, 11 Drawing Figures

METHOD OF REGULATING HORMONE FUNCTION OR RELEASE

This work was supported in part by a grant from the National Institutes of Health and from the Mellon Foundation.

BACKGROUND OF THE INVENTION

1. Field of the Invention

Within the general area of hormone regulation this invention relates to the synthesis and use of synthetic hormone complexes. These complexes have as one component a peptide which confers binding specificity for hormone or regulatory factor receptors on or in a cell and as a second component a structure which alters second messenger mobilization by the cell. Therefore, one aspect of this invention is a synthetic hormone complex which binds to specific receptors on the surface of or in a particular type of cell and causes either an increase or a decrease in second messenger mobilization by the cell. One such second messenger molecule is calcium ion. A change in calcium ion mobilization results in altered cellular function. This ability to alter cell functions includes any physiological response dependent upon the binding of a polypeptide hormone and a change in calcium mobilization. Other physiological references are dependent upon other second messenger molecules such as cyclic adenosine monophosphate or cyclic guanosine monophosphate. Among the many peptide hormones two classes, the releasing or the release inhibiting hormones, are of particular importance since these classes regulates the function of major hormone systems.

2. Description of the Prior Art

Endocrinologists have long desired to be able to selectively regulate the release of specific hormones as they are released from the animals own hormone producing cells. In part it has been possible to administer to the animal supplemental quantities of a desired hormone or hormone analogue, such as insulin or one of the steroid hormones. However, many hormones are either not available in sufficient quantities, too expensive, evoke immune responses or must be administered in such a highly regulated manner that it is not feasable to use them. In addition, there has been no easy or safe method for removing or reducing the effective or actual concentration of one specific hormone produced in vivo. Calcium ion channel antagonists are known to block calcium ion incorporation non-specifically, that is, for all cell types. Such systemic administration of a calcium ion channel inhibitor is often unacceptable since it alters the physiology of all systems and disrupts basic functions necessary for life, although cardiac drugs such as verapamil have been successful. However, the development of a "targeted" calcium inhibitor would be much more acceptable since the systemic concentration would be quite low and only the cell type "targeted" would receive a dosage sufficient to alter its physiology significantly.

Our present understanding of the regulation and control of hormone release indicates there is a central function played by the class of hormones or factors that modulate normal in vivo release of other hormones. These regulatory hormones or factors are referred to as releasing, stimulating or inhibiting hormones or factors. Pituitary gland regulation of hormone release is a particularly well documented example of the importance of these regulatory hormones. The ability to modulate, either up or down, the release of hormones in vivo would provide the endocrinologist with a tool for optimizing the level of specific hormones. Therefore, there is a need for both hormone agonists and hormone antagonists. Such targeted agonists can be used to overcome metabolic blocks caused not by failure of endocrine synthesis, but by failure to release hormone into the blood. Similarly, overactive endocrine function can be specifically blocked through the use of targeted antagonists which block the release of excessive amounts of a specific hormone. Moreover, such methods, if precisely targeted involve in vivo modulation of only one hormone system and are less likely to disrupt general endocrine homeostasis. Such methods might be useful in treating hormonal imbalance or dysfunction causing disesase, regulating fertility, optimizing growth and meat production, compensating for the effects of non-hormonal diseases and partially alleviating some of the side effects of aging.

References which relate to the subject invention are:
1. Conn et al, *Life Sciences U.S.A.*, vol 24: 2461, (1979).
2. Marian et al, *Molecular Pharmacology U.S.A.*, vol 16: 196, (1979).
3. Conn et al, *Endocrinology U.S.A.*, vol 105: 1122, (1979).
4. Conn et al, *Cell Calcium U.K.*, vol 1: 7, (1980).
5. Marian et al, *Life Sciences U.S.A.*, vol 27: 87, (1980).
6. Conn et al, *Endocrinol. U.S.A.*, vol. 107: 2133, (1980).
7. Conn et al, *Nature UK*, vol 292: 264, (1981).
8. Conn et al, *Endocrine Reviews U.S.A.*, vol. 2: 174, (1981).
9. Hazum et al, *Proc. Natl. Acad. Sci. U.S.A.*, vol. 77: 6695, (1980).
10. Conn et al, *Endocrinology U.S.A.*, 109: 1122 (1981).
11. Marian et al, *Molecular Pharmacology U.S.A.*, vol. 19: 399, (1981).
12. Conn et al, *J. Biol. Chem. U.S.A.*, vol. 256: 1098, (1981).
13. Conn et al, *Endocrinology U.S.A.*, 109: 2040 (1981).
14. Conn et al, *Nature U.K.* in press, 1982 "Conversion Of A Gonadotropin Releasing Hormone Antagonist To An Agonist: Implication For A Receptor Microaggregate As The Functional Unit for Signal Transduction."
15. Conn et al, manuscript submitted, 1982 "Potency Enhancement of A GnRH Agonist: GnRH-Receptor Microaggregation Stimulates Gonadotropin Release."

SUMMARY OF THE INVENTION

Methods are provided for producing synthetic hormonal complexes that bind to receptors on cell surfaces or internally and alter calcium ion incorporation or mobilization by the cell. Each type of synthetic hormonal complex contains a component which confers receptor binding specificity. The synthetic hormone complex also contains a component which alters the mobilization of a second messenger by the cell to which it is bound. One such second messenger is calcium ion. A change in calcium ion mobilization, either an increase or a decrease, results in an altered hormonal response by the cell. For regulatory hormones this altered response would be an increase or a decrease in the secretion of the regulated hormone. For nonregulatory hormone this altered response would be a change in the physiological response of the cell.

An object of this invention is the synthesis of synthetic hormone complexes which contain a means for binding to the receptors of a cell and a means for altering the incorporation of calcium ions by the cell.

Another object of this invention is the synthesis of a synthetic hormone complex having binding affinity for a cell receptor and a calcium ion channel inhibitor or antagonist.

Another object of this invention is the synthesis of synthetic hormone complexes containing two or more molecules of receptor binding peptides, which when bound to cellular receptors result in an increase in second messenger mobilization.

A further object of this invention is the synthesis of synthetic hormone complexes containing two or more molecules of receptor binding peptides, which when bound to cellular receptors result in an increase in calcium ion mobilization.

A still further object of this invention is to form a synthetic hormone complex wherein the hormone is gonadotropin releasing hormone or its analogues in combination with a calcium ion channel inhibitor.

Another object of this invention is a synthetic hormone complex wherein the receptor binding proteins each contain a lysine available for crosslink formation.

Still another object of this invention is the formation of a synthetic hormone complex wherein the receptor binding peptide dimers are joined by a bridging molecule, such as an antibody specific for the peptide.

Another object of this invention is a method of regulating hormones or other regulatory factors by administration of the synthetic hormone complex to a cell surface with a resulting change in calcium ion mobilization leading to a change in physiological function.

Another object of this invention is a method of regulating the release of hormones produced within cells by administration of a synthetic hormone complex which when bound to specific receptors on or in the cell, results in an increase in calcium ion mobilization by the endocrine cell thereby altering the release of hormones.

Still another object of this invention is the regulation of fertility in an animal through administration of a synthetic hormone complexes which result in an increase or decrease in hormones regulatory fertility.

A further object of this invention is the regulation of cyclic AMP or other second messenger molecules by the binding of a synthetic hormone complex to the cell receptor, thereby causing the regulation of physiological functions dependent upon the concentration of such second messenger molecules.

The above and other objects are achieved in accordance with the present invention by providing novel synthetic hormone complexes comprising first one or more peptides with cell receptor binding properties and secondly a structure causing an alteration in second messenger mobilization within the cell.

DETAILED DESCRIPTION OF THE PREFERRED EMBODIMENTS

The products of this invention include synthetic hormone complexes which contain one or more peptides conferring binding specificity for hormone receptors on the surface or within a cell. Also in this synthetic hormone complex is a molecule or structure which modulates or changes the rate of mobilization of second messenger molecules, such as calcium ion through the cell membrane. This modulation of calcium ion mobilization may be an antagonist wherein the calcium ion incorporation is inhibited by a calcium ion channel blocker. The complex may alternatively contain multiple copies of the receptor binding peptide arranged in a configuration which results in an increase in calcium ion mobilization or agonist function.

The second messenger may be calcium ion, cyclic adenosine monophosphate (cAMP) or other regulatory molecules causing changes in the activity of protein kinases or phosphates; causing changes in calmodulin binding or activation or inhibition of target regulatory molecules or in other allosteric regulatory cofactors or proteins resulting in a change in enzyme activity or a change in the three dimensional configuration of proteins or other macromolecules effecting a biological response.

Calcium ion mobilization and incorporation are ued interchangably to indicate a change in the second messenger calcium ions released from intercellular storage or incorporated into the intracellular spaces from extracellular fluids.

Any polypeptide hormone, hormone analogue or regulatory factor having specificity for a cell surface or internal receptor can be utilized in this invention. The products and methods of this invention will be divided into the following stages:

I. Preparation of synthetic hormone complexes which function as antagonists.
II. Preparation of synthetic hormone complexes which function as agonists.
III. Utilization of synthetic hormone complexes for regulation of hormone function or release.

I. Preparation of synthetic Hormone Complexes Which Function as Antagonists

Traditional hormone antagonists compete for receptor binding and thereby act to block the action of a hormone, such as inhibiting the hormone-dependent incorporation of calcium. Novel synthetic hormone complexes were prepared which contained a means for binding to the surface of a cell, such as a hormone to a hormone receptor, and means for altering the mobilization of calcium ions by the cell once the synthetic hormone complex ing of the antibody blocks one of the hormone sites in each dimer, however, it results in a conjugate containing two exposed gonadotropin releasing hormone binding sites for the receptor on a pituitary cell surface. The binding of this dimer conjugate results in an increase in calcium incorporation and the release of luteinizing hormone and follicle stimulating hormone as diagramed in FIG. 8. Gonadotropin releasing hormone could also be used to form such a multimer. Other gonadotropin releasing hormone analogues which are used to form agonists hormone complexes are the following:

pyro glutamic acid$^1$-histidine$^2$-tryptophan$^3$-serine$^4$-tyrosine$^5$-lysine$^6$-lecuine$^7$-arginine$^8$-proline$^9$-glycine$^{10}$-NH$_2$;

D-pyro glutamic acid$^1$-histidine$^2$-tryptophan$^3$-serine$^4$-threonine$^5$-lysine$^6$-leucine$^7$-arginine$^8$-proline$^9$ (ethylamide)-des-glycine$^{10}$;

D-pyro glutamic acid$^1$ D-phenylalanine$^2$-tryptophan$^3$-serine$^4$-threonine$^5$-D-lysine$^6$-leucine$^7$-arginine$^8$-proline$^9$-glycine$^{10}$-amide.

Figure 4:
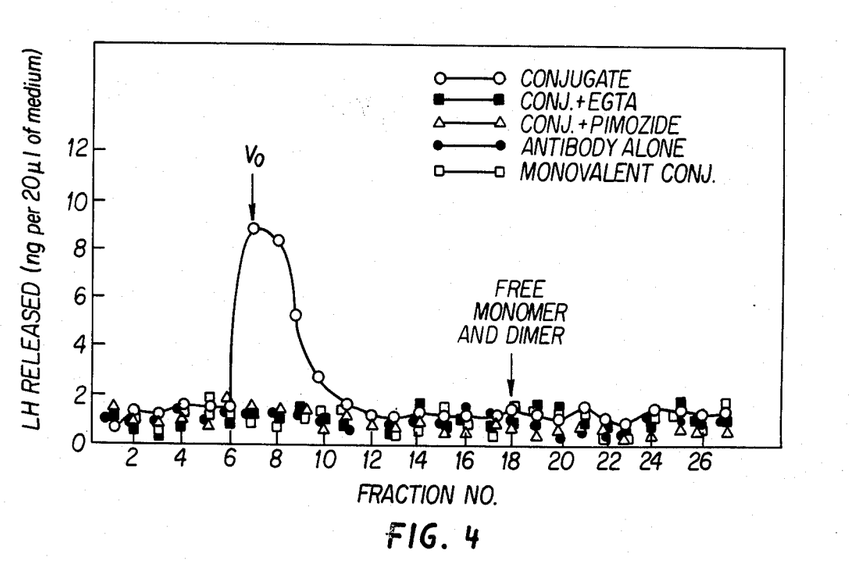
FIG. 4 Gel filtration of Synthetic Hormone Complex and stimulation of Luteinizing Hormone Release on Pituitary Cells in culture (Agonist function). Complex here is conjugate of 2 dimers (GnRH-ANT)$_2$ conjugated by antibody. EGTA and Pimozide block calcium dependent stimulation of LH release.Luteinizing Hormone release by pituitary cell cultures as a function of Gonadotropin releasing hormone analogue concentration. Antagonist function measured with and without added $10^{-7}$M GnRH.
Figure 11:
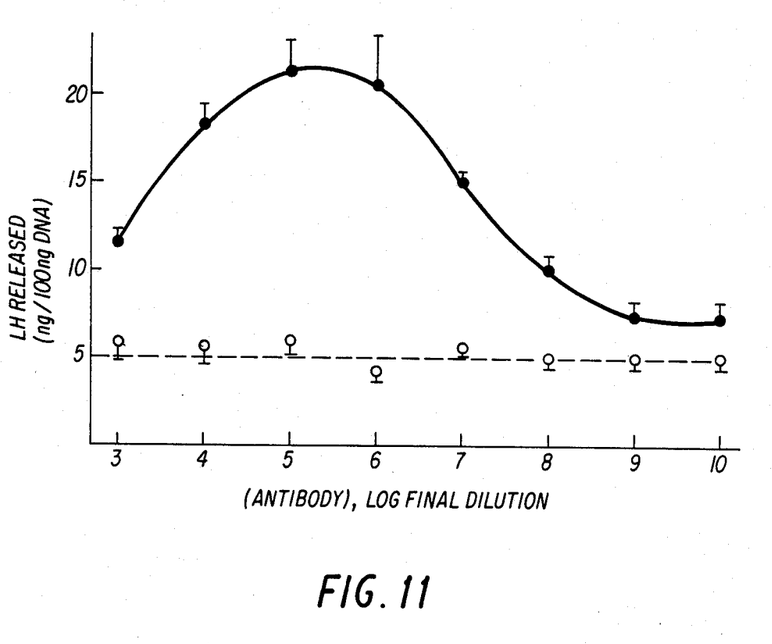
FIG. 11—Potentiation of Action of (D-Lys$^6$-GnRH)$_2$-EGS dimer by addition of antisera (solid symbol). Antisera alone is shown by open symbol.

The agonist function of the synthetic hormone complex or conjugate is illustrated in FIG. 4. The conjugate stimulates the release of LH from pituitary cells and cultures, while the unconjugated monomers and dimers do not stimulate LH release. Therefore, the formation of the conjugate with the spacer molecule is necessary to create the agonist function. FIG. 11 similarly illustrates the formation of agonists through dimer-antibody conjugate formation.

Figure 8:
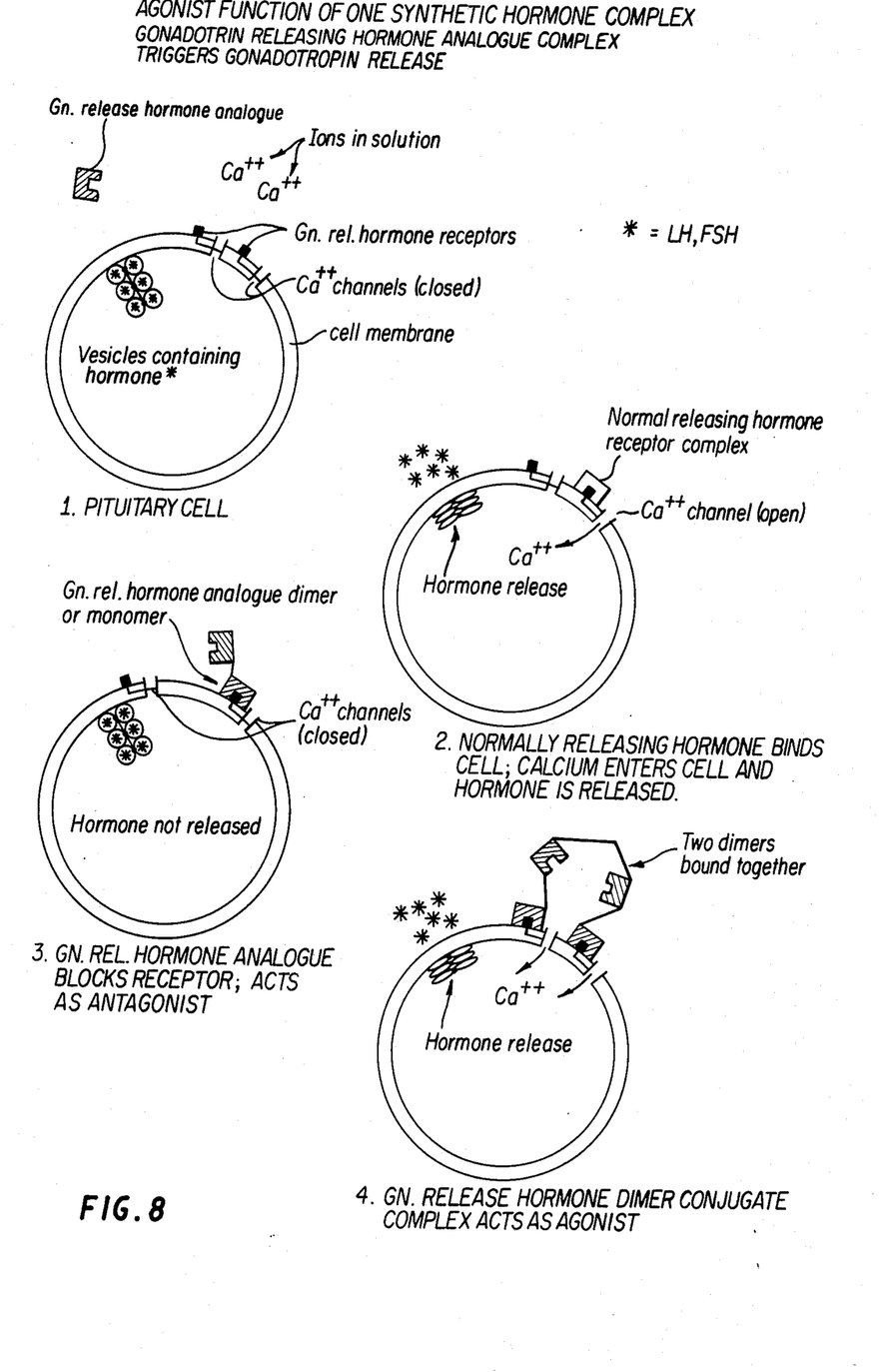
FIG. 8—Agonist function of one synthetic hormone complex. A diagrammatic scheme for a gonadotropin releasing hormone complex containing 2 gonadotropin analogue dimers bridged by 150 Å connecting molecule.

While a D-lysine in the 6 position is used to form the dimer in the gonadotropin releasing hormone model system, it is recognized that there are other procedures whereby dimers of hormones or hormone analogues can be formed. Such dimers might be formed between free sulfhydryl groups, between glutamic acid side chains and lysine side chains or a bifunctional spacer molecule could be used to form the connection. In FIG. 8 the resulting dimer conjugate bound by antibody results in a distance of approximately 150 angstroms between the hormone receptor binding sites. However, it is recognized that in some situations with this or other hormones, a distance of between 50 and 300 angstroms may be utilized. The bridging molecule may be antibody such as immunoglobulin G, immunoglobulin A or immunoglobulin M. In the example diagramed in FIG. 8 the antibody used to form the dimer conjugate was immunogobulin G with binding specificity for the D-lysine$^6$ region of the gonadotropin releasing hormone. It is recognized that a dimer conjugate is only one of many possible multimers of the homone which will stimulate the incorporation of calcium into a cell. These hormone multimers may be formed using antibody or any other bridging molecule, such as one or more covalent cross-links 50 to 300 angstroms in length. It is also recognized that a hormone multimer may be formed using a polyvalent antibody such as IgM. It is also recognized that polyvalent antibody complexes can be formed by aggregation or complexing of multiple divalent antibody molecules.

Figure 7:
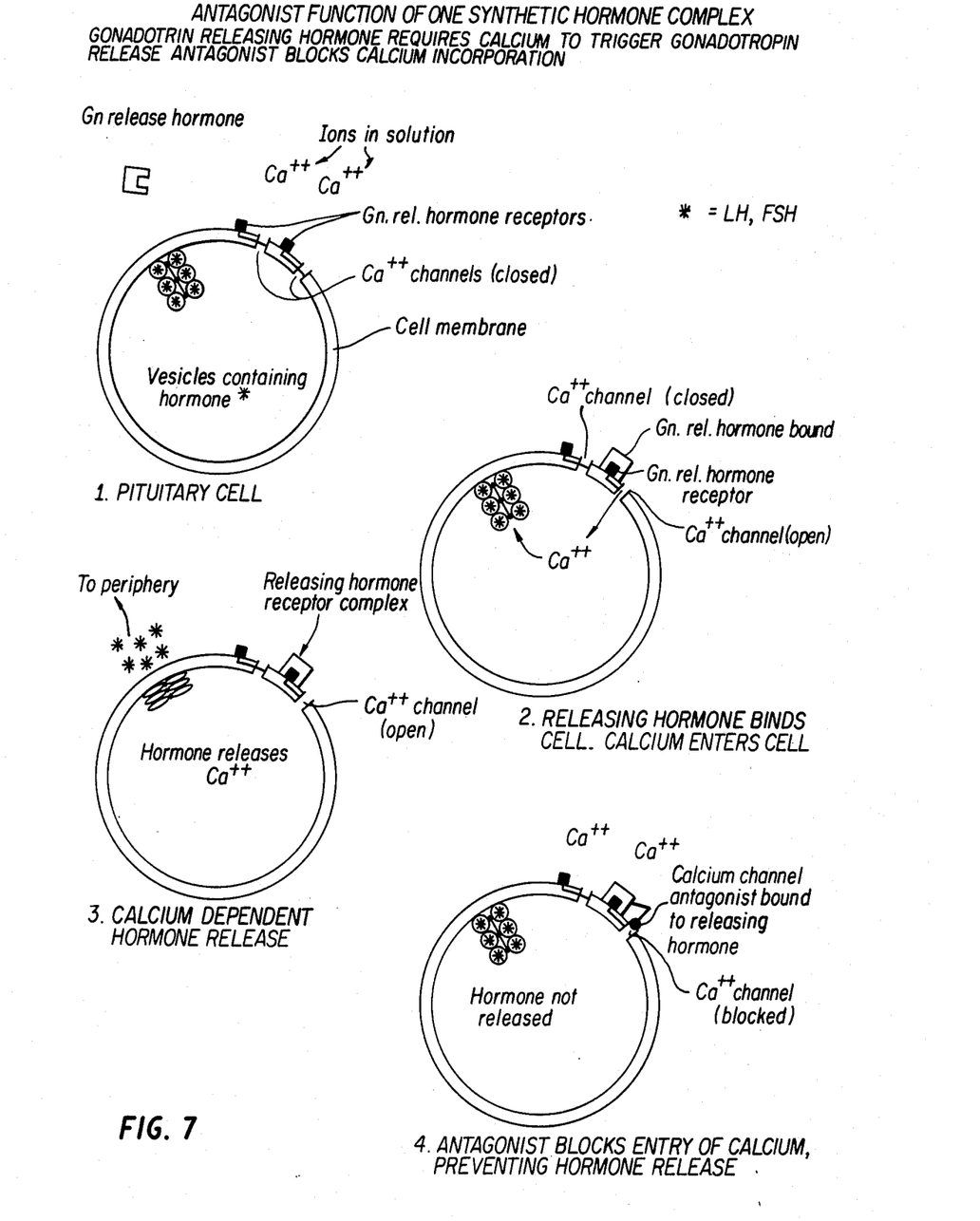
FIG. 7—Antagonist function of one synthetic hormone complex. A diagrammatic scheme for a gonadotropin releasing hormone complex containing a calcium ion channel inhibitor.

III. Utilization of Synthetic Hormone Complexes for Regulation of Hormone Function or Release Most polypeptide hormones first come in contact with the outer surface of a cell, and if an appropriate receptor is present, the hormone will bind to the cell surface and trigger a physiological response. One method by which such a physiological response is catalyzed is through the stimulation of a second messenger molecule such as calcium ion mobilization. Therefore, the ability to pharmacologically regulate the incorporation of calcium ions in specific cells permits the regulation of a hormone's physiological response in that cell. Conceptually, there are two ways in which calcium ion incorporation can be regulated, that is an increase or a decrease. In FIG. 7, there is a diagrammatic representation of the antagonist function of one synthetic hormone complex. That is, the inhibition or decrease in the incorporation of calcium ions. In this example, the gonadotropin releasing hormone normally triggers incorporation or mobilization of calcium ion, this is, unless an antagonist blocks such calcium ion incorporation. In FIG. 7, diagram 1, illustrating a pituitary cell, we see a cell containing vesicles which store the hormones LH and FSH. On the surface of the cell there are located gonadotropin releasing hormone receptors, and in close proximity calcium ion channels in the closed position. In solution exterior to the pituitary cell are located free calcium ions. In the second diagram of FIG. 7, we see the releasing hormone binding to the receptor causing the calcium ion channel to become permeable to calcium ions. This calcium ion incorporation by the pituitary cell results in the release of hormones to the cells periphery, shown in diagram 3 of FIG. 7. In diagram 4 of FIG. 7, we see an antagonist blocking entry of calcium ions and therefore, blocking the release of LH and FSH from the pituitary cell. This antagonist function results from the synthetic hormone complex containing one component which binds specifically to the pituitary cell surface hormone receptor, and a second component which is a calcium ion channel antagonist. This antagonist blocks the calcium ion channel and does not permit the incorporation of the calcium ions. It also blocks the binding of a normal gonadotropin releasing hormone to the receptor.

The agonist function of a synthetic hormone complex is illustrated in FIG. 8. Diagram 1 of FIG. 8 shows a normal pituitary cell which contains the hormones LH and FSH. On the cell surface are specific receptors for gonadotropin releasing hormone and in adjacent areas calcium ion channels in the closed position. The calcium ions in solution cannot pass through the cell membrane unless the channels are open. In diagram 2 of FIG. 8 we see the normal physiological situation wherein the gonadotropin releasing hormone binds to its cell surface receptor, triggering the calcium ion channel opening and the incorporation of calcium ions. The increase in calcium ion concentration triggers the release of the hormones LH and FSH to the medium surrounding the cell. In diagram 3 of FIG. 8 the gonadotropin hormone analogue dimer binds to a cell surface receptor but does not open the calcium ion channel. Therefore, calcium ions cannot enter the pituitary cell and the analog functions as an antagonist preventing the release of the hormones LH and FSH. In diagram 4 of FIG. 8, two gonadotropin releasing hormone analogue dimers are complexed together. They bind to the gonadotropin receptor on the pituitary cell surface and now trigger the incorporation of calcium ions. This incorporation of calcium ions causes the release of the hormones LH and FSH. Therefore, the complex formed by the two dimers bound together surprisingly have the ability to function as an agonist.

Other polypeptide hormones or their analogues can be substituted in the agonist complex described in FIG. 8. They will have a similar function on those cells which contain the specific cell surface receptor for their binding. Therefore, any cell function regulated by the incorporation of calcium ions triggered by the binding of a hormone to a cell surface receptor can be used in a agonist complex similar to that described in FIG. 8.

The antagonist function of FIG. 7 illustrates a method for inhibiting the release of hormones by an endocrine cell. In FIG. 7, the release of the fertility hormones LH and FSH was inhibited through the use of a synthetic hormone complex with specificity for the gonadotropin releasing hormone receptors.

The agonist function of FIG. 8 illustrates a method for increasing the release of hormones by an endocrine cell. In FIG. 8, the release of the fertility hormores LH and FSH was stimulated through the use of the synthetic hormone complex with specificity for the gonadotropin releasing hormone receptors.

Other polypeptide hormones, hormone analogues or releasing factors can be used in a similar manner to that illustrated in FIGS. 7 and 8 to bind to their respective cell surface receptors and block or stimulate incorporation of calcium ions. The following is a list of additional regulatory hormones which control the release or secretion of other hormones:

corticotropin releasing hormone;
growth hormone releasing hormone;
thyrotropin releasing hormone;
prolactin releasing hormone;
melanocyte stimulating hormone releasing hormone;
growth hormone release inhibiting hormone; (Somatostatin);
prolactin release inhibiting hormone;
melanocyte stimulating hormone release inhibiting hormone;
gonadocrinin;
ganadostatin; and
somatomedin.

Each of the above hormones or their analogues can be used in a synthetic hormone complex in a manner analogous to that illustrated in FIG. 7 or 8.

It is recognized that other releasing hormones or release inhibiting hormones can also be used in such a similar situation.

The antagonist or agonist method of regulating the release of hormones from endocrine cells can be used both in vitro through incorporation into the tissue culture medium, or in vivo through administration of the synthetic hormone complex in a pharmacologically effective amount. One method of regulating fertility is the application of the synthetic hormone complex containing the gonadotropin releasing hormone analogue complex as an antagonist, thereby preventing the release of luteinizing hormone or follicle stimulating hormone. This inhibition of LH and FSH results in a decrease in fertility. Similarly, the use of a synthetic hormone complex containing multiple hormone subunits functions as an agonist, thereby increasing fertility. Therefore, depending upon whether an agonist or an antagonist is utilized it is possible to either increase or decrease fertility. Each of the above-named polypeptide regulatory hormones can be used in a similar manner, that is, either in an antagonist complex or an agonist complex, facilitating the regulation of their respective hormone releasing properties.

Some polypeptide hormones regulate physiological responses other than or in addition to the release of hormones. Among these polypeptide hormones are included the following: follicle stimulating hormone, luteinizing hormone, prolactin, growth hormone, thyroid stimulating hormone, adrenal corticotropin, melanocyte stimulating hormone, parathyroid hormone, calcitonin, relaxin, vasopressin oxytosin, insulin, glucagon, erythropoietin cholecystokinin, gastrin and angiotensin. These polypeptide hormones or their analogues can be used in a manner similar to that described for gonadotropin releasing hormone. That is, each of these polypeptide hormones can be used as an antagonist by attachment of a calcium ion channel inhibitor or an antagonist. Each of the above polypeptide hormones can be used as an agonist by complexing with antibody or other bridging molecules such that multiple receptors can be bound resulting in an agonist function.

Applicant does not wish to be bound by an theory of action, such as those expressed in FIGS. 7 and 8. Other mechanisms of action not now recognized may, in whole or in part, be responsible for the antagonist or agonist properties described for the synthetic hormone complexes. In particular, the synthetic hormone complexes may action via receptors external or internal. The second messenger molecule is not limited to calcium ion, cAMP, cGMP or other known second messenger.

Having now fully described the invention, it will be apparent to one of ordinary skill in the art that many change and modifications may be made without departing from the spirit of the invention as set forth herein.

EXPERIMENTAL EXAMPLES

EXAMPLE 1

Figure 1:
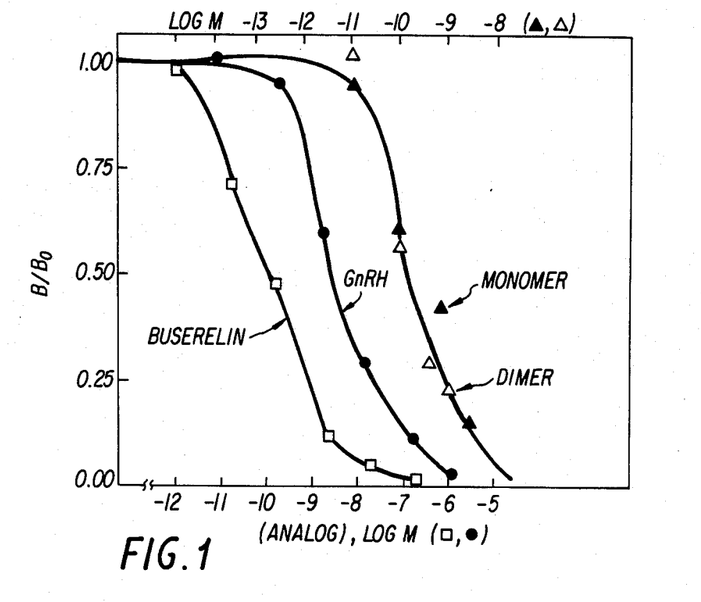
FIG. 1—Competitive Binding to Receptor Sites of Pituitary Plasma membrane in the presence of unlabeled Buserelin, Gonadotropin Releasing Hormone (GnRH), GnRH-Antagonist monomer (GnRH-ANT) and GnRH-Antagonist dimer ethylene glycol bis(succinimidyl succinate) (EGS).

Ability of gonadotropin releasing hormone antagonist to complete for binding to gonadotropin releasing hormone receptor One measure of a hormone's properties is its binding affinity to its receptor. FIG. 1 illustrates the relative binding affinities for the gonadotropin releasing hormone sites on a plasma membrane fraction from the rat pituitary. Buserelin is a well established ligand for the gonadotropin releasing hormone receptor. [125-I]-Tyr$^5$-D-ser(tert-butyl)$^6$-desGly$^{10}$-Pro$^9$ethylamid-GnRH ([125-I] Buserelin, Hoechst Pharmaceuticals) binds to the gonadotropin releasing hormone receptor sites on the plasma membrane. The ability to compete with the iodine labelled Buserelin indicates the relative affinity for the receptor. Unlabelled Buserelin displaces about 50% of the labelled Buserelin at $10^{-10}$ molar as illustrated in FIG. 1. The data are expressed in terms of equivalents of releasing hormone analogue showing the radioligand bound in the presence of the indicated analogue concentration (B) compared to that bound in the absence of added analog ($B_o$).

Binding Assay

The binding assay was conducted in polypropylene microfuge tubes which were precoated overnight with 1% BSA. The assay contained approximately 20,000 cpm of $^{125}$I-labeled Buserelin and 30 μg of membrane protein, in the presence or absence of $10^{-5}$M GnRH. In some competition experiments, the amount of added GnRH was altered as indicated. To determine the specificity of binding, des-pGlu$^1$-GnRH (Bachem, Torrance, Calif.), D-Ala$^6$-GnRH (Peninsula Laboratories, Inc., San Carlos, Calif.), D-Phe$^2$-D-Ala$^6$-GnRH (Wyeth Laboratories, Philadelphia, Pa.) TRH (Peninsula Laboratories), arg$^8$-vasopressin (Calbiochem, San Diego, Calif.), or somatostatin (Beckman Instruments, Fullerton, Calif.) were added at the indicated concentrations.

The final assay volume was 500 μl adjusted with 10 mM Tris-0.1% BSA. Following a 2-hr incubation on ice, bound and free hormone were separated by centrifugation. (Eppendorf microfuge, 12,800×g, 5 min) through 100 μl of 10% (w/v) sucrose. The tips of the tubes were cut off and radioactivity was determined by γ-spectroscopy. Most (80-85%) of the membrane-bound radioactivity was displaceable by excess competing ligand. Less than 1.5% of the total added radioactivity, or about 10% of the nondisplaceable counts, were found to bind to the tube tip itself (assayed in the absence of any membrane). For some kinetic studies, bound hormone and free hormone were separated by the method of rapid filtration. Incubations were performed in triplicate. Specific binding was determined by subtracting nonspecific binding (in the presence of excess unlabeled GnRH) from total binding (no GnRH). Scatchard analysis of the binding data, using linear regression analysis to establish best-line fit, was used to determine the number and binding affinity of GnRH receptors. The t-test was used to determine significance of differences. Membrane fractions prepared from groups of animals killed at different times were assayed in two or more binding studies with different batches of radiolabel, to distinguish results to assay variability. Since results were similar regardless of the batch of radiolabel used and between the groups of animals, data in such cases were pooled and are expressed as means ± standard error of the mean.

The natural gonadotropin releasing hormone binds less well to its own receptor than Buserelin with 50% of the Buserelin displaced when the gonadotropin releasing hormone is approximately five times $10^{-9}$ molar. Gonadotropin releasting hormone-antagonist (D-pyroglumatic acid-D-phenylalanyl-D-tryptophanyl-D-lysyl-GnRH binds to the gonadotropin releasing hormone receptor with higher affinity than natural sequence releasing hormone. FIG. 1 illustrates the binding affinity of both the GnRH-antagonist monomer, and the EGS-linked GnRH-antagonist dimer. Both the GnRH-antagonist and the EGS dimer displaces binding with about 50-fold less affinity than the natural sequence gonadotropin releasing hormone. When expressed in terms of equivalence of monomeric hormone, both the monomer and dimer had similar activity, suggesting that the GnRH-antagonist dimer components behave as two independent ligands at the receptor. The binding displacement assay is not sufficiently sensitive to detect the additional contribution in molecular weight (about 10%) due to the EGS chain. The GnRH antagonist inhibits the GnRH-stimulated ($10^{-9}$ molar) gonadotropin release from pituitary cultures with the 50% inhibitory concentration $(IC_{50})=2\times10^{-10}$ molar. The GnRH-antagonist has no measurable antagonist activity; the presence of the D-lysine[6] both affords protection against proteolysis and introduces a single amino acid group into this molecule which may be used for derivation without loss of receptor binding activity. The formation of the GnRH-antagonist dimer by cross-linking of the lyslamino groups of two molecules with ethylene glycol bis(succinimidyl succinate) (EGS) results in a GnRH-antagonist dimer joined through a 12-15 angstrom chain. Like the parent compound, this dimer is purely an antagonist. It competes with the gonadotropin releasing hormone for its receptor on the pituitary cell surface. However, its binding affinity is higher than that of the natural gonadotropin releasing hormone.

Example 2

Figure 2:
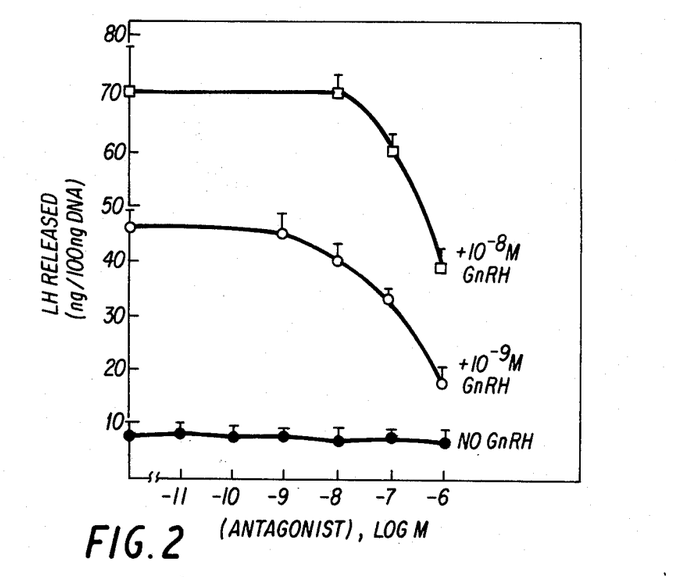
FIG. 2—Luteinizing Hormone Released from Pituitary Cells in Culture As a Function of GnRH-Antagonist Concentration in the presence of none, $10^{-9}$ or $10^{-8}$ Molar GnRH.

Ability of gonadotropin releasing hormone antagonist to inhibit gonadotropin releasing hormone stimulated LH release from pituitary cell cultures FIG. 2 illustrates the ability of the gonadotropin releasing hormone antagonist to inhibit gonadotropin releasing hormone-stimulated LH release from pituitary cell cultures. Luteinizing hormone release from pituitary cell cultures is dependent upon the binding of the gonadotropin releasing hormone to its specific cell surface receptor. The GnRH-antagonist binds to this receptor and blocks stimulation by GnRH. GnRH-antagonist alone has no detectable agonist action up to $10^{-6}$ molar as illustrated in FIG. 2. The presence of the GnRH antagonist blocks the action of both $10^{-8}$ molar and $10^{-9}$ molar GnRH. In FIG. 2 the antagonist activity of GnRH-Ant was measured in a cell culture bioassay. Two day pituitary cell cultures were incubated with $10^{-8}$M, $10^{-9}$M, or no GnRH at the indicated concentration of antagonist. After the 5 h incubation period, the medium was assayed for LH by RIA using rat LH antisera (LHS-4), highly purified rat LH for labeling (LH I-4), and rat LH standard (LH-RP-1) which were made available by a grant from the NIAMDD Hormone Distribution Office (prepared by Dr. A. Parlow, Torrance, CA.). The assay was performed as described below, except that second antibody was used to separate the bound and free [$^{125}$-I]-LH.

Standard Assay

Cell cultures were prepared, by collagenase-hyaluronidase dispersion of pituitaries from 25-day-old female weanling rats. The cultures were then incubated for 2 days at 37 C. in culture plates. Each well had a maximum volume of 2.2 ml, and cells were added in a volume of 1.0 ml. After the culture period, the cells were washed free of debris and sera with medium 199 containing 0.3% bovine serum albumin (Cohn fraction V; 199/BSA) and incubated with the indicated compounds. Medium 199 normally contains 1 mM $Ca^{2+}$. Cells were incubated in 1.0 ml medium for 3 h. After the incubation period, the supernatant fraction was removed from the cells (attached to the culture dish) with a Pasteur pipette and assayed for LH by RIA employing rat LH antisera (LHS-5), highly purified rat LH for labeling (LH-I-6), and rat LH standard (LH-RP-1), all of which were made available by the NIAMMD Hormone Distribution Office and were prepared by Dr. A. Parlow (Torrance, CA). The assay was performed, using immobile protein A to separate the bound and free [$^{125}$I]LH. The intraassay variance was 7%, and the interassay variance was 12%. LH release was normalized by DNA determination in order to correct for slight differences in cell numbers in different assay wells.

Example 3

Gel filtration demonstrates molecular weight of agonist complex

Figure 3:
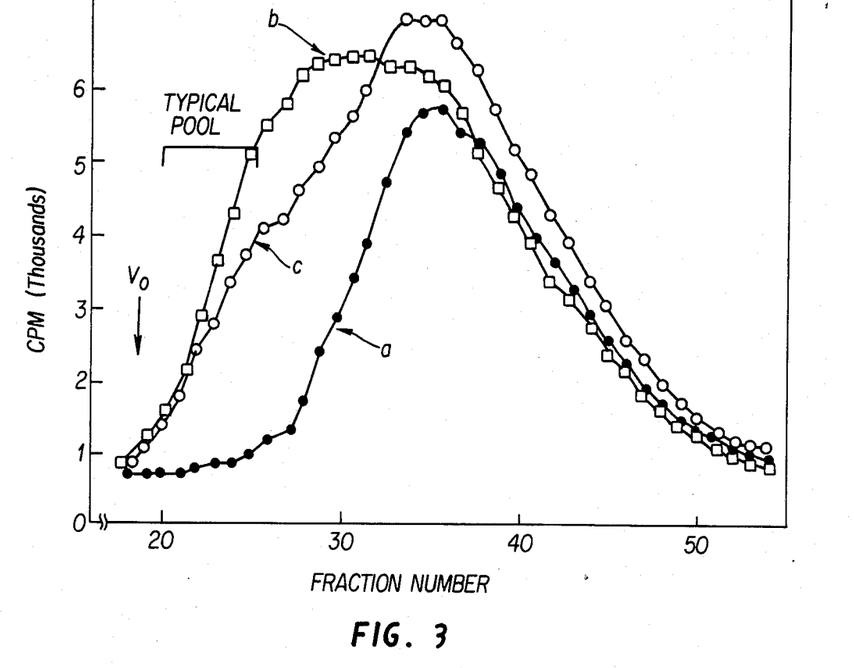
FIG. 3 Gell filtration (Sephadex G25) Elution Pattern of (a) Authentic [$^{125}$I]-GnRH-ANT; (b) EGS+GnRH-ANT dimerization mix, (c) same as (b) but dimerization at 1/10 concentration of (b).

The elution pattern from Sephadex G-25 gel filtration chromatography is illustrated in FIG. 3. Profile (a) is a profile of the authentic [125-I]-GnRH-Ant. Gel chromatography pattern (b) is that of the EGS+GnRH-Ant dimerization reaction mix and (c) is the EGS+GnRH-Ant dimerization mix when the cross-linking volume was tenfold greater than in (b). In general, the larger the molecular weight the earlier the complex is eluted from the gel filtration column. Although complete separation of the monomer and the dimer was not possible, the leading edge (See bracket in FIG. 3) consisted of fractions of GnRH-Ant dimer which contained less than 0.5% monomer. In order to provide evidence for the formation of a dimer, EGS cross-linking was performed in a tenfold greater than normal incubation volume (a condition which would not favor the two second order reactions required for the formation of the GnRH-Ant dimer). As shown in FIG. 3, this resulted in an elusion pattern in which a smaller percentage of the total GnRH-Ant was cross-linked by EGS, illustrated by the greater magnitude of the profile (b) fractions 23 through 31.

Experimental Procedure

GnRH-Ant was iodinated using chloramine T. Free $^{125}I$ and unlabeled hormone were removed from the GnRH-Ant by carboxymethyl cellulose column chromatography, with the labeled analog eluted from the column with 20 mM sodium phosphate, pH 4.5. Maximum binding (assessed by binding with excess GnRH antiserum (No. 9113)), ranged from 89-92% in different preparations and specific activity (assessed by self-displacement assay with pituitary plasma membrane) was approximately 1 mCi/$\mu$g. The product was stored in the elution buffer at 4° C. for up to two weeks. At that time, >90% of the hormone (in different preparations) was intact as judged by electrophoresis. 10 nmoles of GnRH-Ant in 10 $\mu$l of 10 mM sodium phosphate (pH 8.5) and 20 $\mu$l (approximately 0.05-0.15 $\mu$Ci) of [$^{125}$I]-GnRH-Ant in 200 mM sodium phosphate (pH 8.7) were combined with 5 nmoles of ethylene glycol bis(succinimidyl succinate), (EGS, Pierce Chemical Company, Rockford, ILL.) in 1.5 $\mu$l of dimethylsulfoxide (DMSO, redistilled from Fisher). The EGS was stored in the dark at $-70°$ C. and was dissolved in DMSO immediately prior to use. EGS has 2 moles of reactive groups per mole; accordingly, the reactive groups were present in equimolar concentration with the lysyl epsilon amino in GnRH-Ant. After 1 h at 18° C. the reaction was terminated by dilution with 270 $\mu$l 40% ethanol, 10 mM sodium phosphate (pH 8.5) and immediately applied to a G-25 column (10×260 mm) previously equilibrated in the ethanolic buffer. Positions of eluting substances were determined by radioactivity and confirmed by RIA (using antibody No. 9113 at final titre of 1:7,000, radioiodinated GnRH, and authentic GnRH-Ant standard).

Example 4

Gel filtration of synthetic hormone complex and agonist function

The agonist function of a synthetic hormone complex or conjugate is illustrated in FIG. 4. The release of luetinizing hormone by pituitary cells in culture is dependent upon the stimulation of gonadotropin releasing hormone. A synthetic conjugate containing two dimers, each dimer containing two GnRH-Ant joined by EGS. The conjugate consist of two such dimers joined by antibody specific for the GnRH-Ant. This conjugate elutes from the gel filtration column in the void volume ($V_0$) and has the ability to stimulate LH release from pituitary cells in culture. In contrast to the GnRH-Ant alone, the conjugate displayed agonist action, causing the release of 9 ng LH/20 $\mu$l of medium compared to 0.8±0.1 ng LH/20 $\mu$L medium for basal release and 13.6±0.9 ng LH/20 $\mu$L of medium released in response to $10^{-7}$ moles GnRH during a five hour period. This stimulated release was blocked by 2 mM EGTA (in the presence of "normal" 1.25 mM extracellular calcium) and by five micromolar Pimozide (which behaves as a calmodulin antagonist in this system). In addition, the antibody alone (FIG. 4) of the GnRH-Ant dimer alone did not stimulate measurable release (0.9±0.1 ng LH/20 $\mu$l medium). The reduced pepsin antibody fragment (i.e. monovalent antibody) conjugated with the GnRH-Ant dimer did not stimulate release indicating the requirement for at least bivalency to produce this effect.

The Procedure for Demonstrating the Assay

Effect of column fractions containing the antibody-dimer conjugate on LH release from pituitary cell cultures was as follows. 120-160 ng (GnRH-Ant)$_2$-EGS collected from the leading edge of the G-25 column described for FIG. 3 (which contained <0.5% of the free GnRH-Ant (or EGS-GnRH-Ant monomer complex, estimated from other column eluant patterns)) was lyophilized in a glass tube. Rabbit anti-D-Lys$^6$-GnRH (antiserum No. 5111 prepared by immunization with D-Lys$^6$ coupled to bovine serum albumin (BSA) with glutaraldehyde) was added without additional purification in an amount sufficient to bind 8-10% of the dimer. The antibody was added in a final volume of 50 $\mu$l (with Medium 199 containing 0.3% BSA and 2 mg NaN$_3$). The reaction ws allowed to proceed 10 h at room temperature and then 2 days at 10° C. Immediately before the cell bioassay, the solution was applied to a 12 ml calibrated G-75 column (10×260 mm) equilibrated in 199/BSA. Twenty drop fractions (about 300 $\mu$l) were collected and brought to 1.0 ml with 199/BSA. The conjugate elutes in the $V_o$. Where monovalent antibody is specified, the reduced pepsin fragment of antibody (No. 5111) was substituted for intact antibody in the conjugation described above. In this case ammonium sulfate fractionated IgG was dissolved in 50 mM acetate buffer, pH 4.5 and digested with pepsin (Worthington Biochemical Corp.) at an enzyme:substrate ratio of 1:100 for 50 min at 70° C. Digestion was stopped by neutralization with 1M Tris-HCL, pH 8.0 and 0.1N NaOH. Precipitated material was removed by centrifugation and 2-mercaptoethanol added to the supernatant at a final concentration of 0.75 mM. The solution was maintained at room temperature for 1 h, then cooled in ice cold water. An equal volume of 0.75 mM iodoacetamide (previously degassed and cooled to 4° C.) was added and triethanolamine added to maintain the pH at 8.0±0.2. After 1 h the solution was dialyzed against 3 changes (2 h each) of 100 vol ech of 0.9% NaCl then lyophilized. This product was more than 95% cleaved as judged by the inability to precipitate [$^{125}$I-]-D-Lys$^6$-GnRH with protein A. Cell cultures (described in FIG. 1) were incubated with the column fractions in a final volume of 1.0 ml of Medium 199 containing 0.3% BSA. The conjugate (N=7, O—O ) stimulates LH release, (by RIA as described for FIG. 1) which is blocked in the presence of 10 $\mu$M Pimozide (N=3, △—△ ) or 2 mM EGTA (N=3, ■—■ ). Conjugate prepared with monovalent antibody (N=3, □—□ ) or bivalent antibody alone (N=3, ●—● ) did not stimulate release. Standard errors of the means, which are not shown for graphic clarity, were <15% of the indicated value.

The formation of the GnRH-Ant dimer by cross-linking of the lysineamino groups of two molecules of ethylene glycol bis (succinimidyl succinate) results in the GnRh-Ant dimer joined through a 12-15 angstrom connector. Like the monimer parent compound, this dimer is purely an antagonist. When antibody (AB) to the D-lysine⁶-GnRH (which cross-reacts with the GnRH-Ant) is incubated with excess dimer, a product is formed which consists of a divalent antibody with a GnRH-Ant dimer attached to each arm. This conjugate structure is the following (AB-((GnRH-Ant)-EGS-(GnRH-Ant))₂). One molecule of each GnRH-Ant dimer is attached to the antigenic binding site of the antibody and it is therefore unavailable for receptor binding. The other molecule of each hormone dimer is available for binding to the receptor although still bound to the antibody via the 15 angstrom chain which attaches the two parts of the dimer. Thus, the product consists of two molecules of GnRH-Ant available to the receptor although separated from each other by about 150 angstroms.

In contrast to the parent compounds, this conjugate is an Agonist, stimulating the release of LH from pituitary cell cultures. This release is calcium dependent and is blocked by the anti-calmodulin drug, Pimozide (Janssen Pharmaceutical). Conjugates prepared from monovalent antibody fragments do not stimulate LH release; neither the hormone dimer or antibody alone stimulate LH release. Therefore, a pure Antagonist becomes an Agonist when it is capable to bringing two receptor molecules within a critical distance, 15 angstroms to a 150 angstroms. Distances as short as 10 angstroms and as great as 300 angstroms may also result in active Agonist function. The data indicate that the formation of the receptor microaggregate itself is sufficient to stimulate a transmembrane response system which requires the presence of calcium. Thus, while Agonists and Antagonists may both bind to similar sites on the receptor, the latter is unable to produce this active functional unit. The GnRH-Ant dimer possess only a 15 angstrom separation which appears to be inadequate to bridge receptor binding sites; accordingly, it cannot stimulate release. The added length, due to the antibody, indicates that the correct bridge length is in the range of 150 angstroms.

It is unlikely that the releasing hormone itself bridges two receptor sites since it is neither multivalent or sufficiently long to due so. A more likely possibility is that receptor occupancy by an Agonist alters the receptor structure in such a way as to increase the probability of microaggregation. For example, occupancy by an Agonist might increase the freedom of mobility of the receptor in the plasma membrane by releasing it from an anchoring attachment. Alternatively, a confirmational change might occur such that complementary binding sites are exposed. It is also possible that occupancy activates enzymes which catalyze the formation of di-sulfide or peptide bonds and thereby link receptors. An antagonist would be viewed as occupying the binding site without effecting these changes.

Example 5

Figure 5:
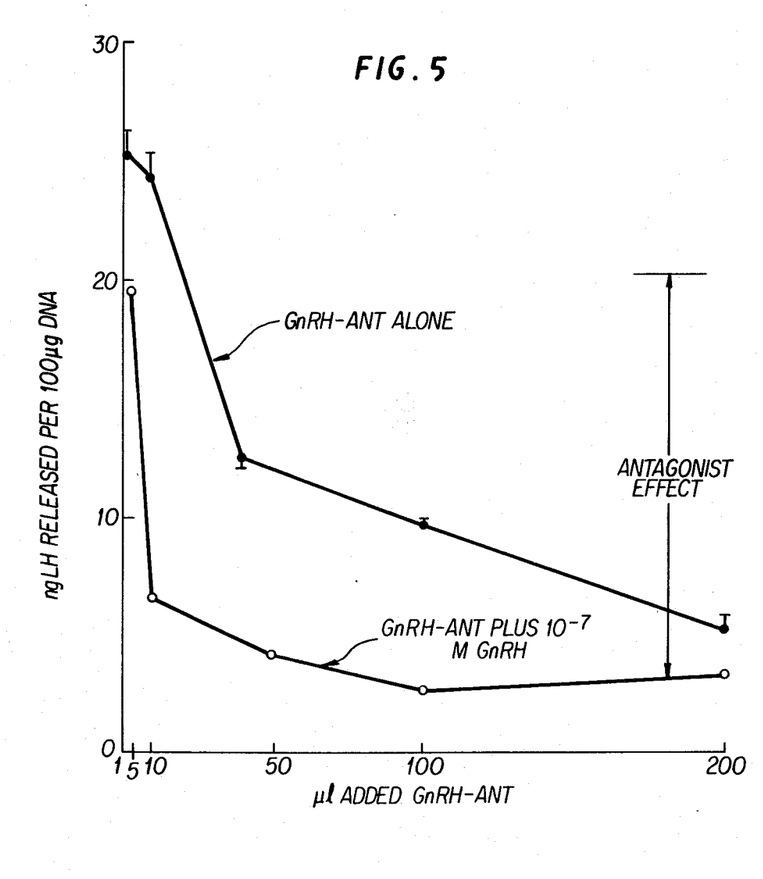

Antagonist function of synthetic gonadotropin releasing complex on pituitary cells in culture A synthetic hormone complex containing a gonadotropin releasing hormone and a calcium ion antagonist were incubated with pituitary cells in culture and the release of Lutenizing hormone measured. The Luteinizing hormone released was standarized per hundred micrograms pituitary cell culture DNA. The pituitary cell cultures were prepared as described in Example 2. The amount of GnRH-Ant added is in $\mu l$ of an unknown concentration. In FIG. 5 with GnRH-Ant alone, note that there is some agonism at low concentrations where the D-Lys⁶-GnRH action can be seen. In the lower curve of FIG. 5, a second incubation with $10^{-7}M$ GnRH was performed to demonstrate the antagonist activity. The exact concentration of GnRH-Ant can be determined by high pressure liquid chromatography.

The antagonist used in FIG. 5 contained the calcium ion channel inhibitor shown below and was prepared in the following manner:

If increased bridge lengths are needed, $H_2N(CH_2)_nCOOH$ is inserted to yield $$NH-\overset{S}{\underset{\|}{C}}-NH(CH_2)_nCOOH$$

at the substitution site. This site is then condensed with D-Lys⁶GnRH.

The release of Luteinizing hormone was measured in the presence and in the absence of normal gonadotropin releasing hormone ($10^{-7}$ more). The $10^{-7}$ molar gonadotropin releasing hormone is a hundredfold in excess of the $K_d$. This was an attempt to mimic the naturally occurring hormone surge. It should be noted that the antagonism was maintained even in the presence of the natural hormone. The Antagonist effect is that decrease in LH released by the cell in the presence of the Antagonist relative to that which was released in the presence of hormone.

Example 6

Figure 6:
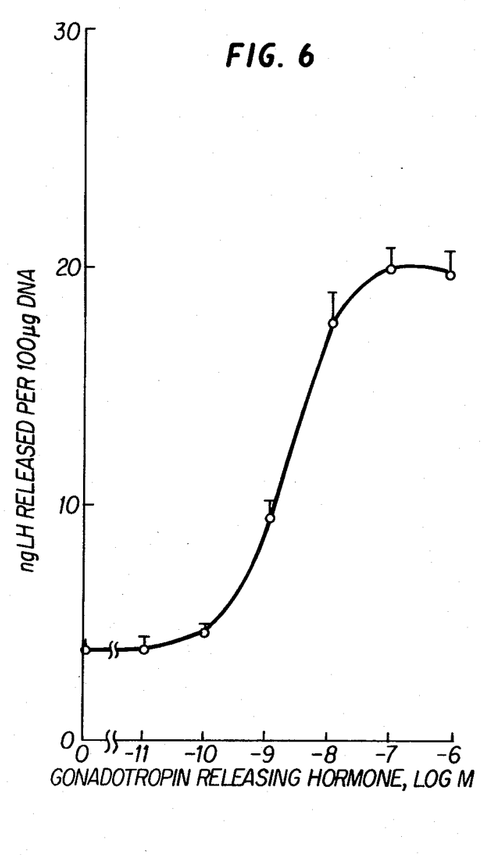
FIG. 6—Gonadotropin releasing hormone stimulation of Luteinizing Hormone release from pituitary cells in culture.

Gonadotropin releasing hormone stimulation of LH release from pituitary cells in culture The ability of gonadotropin releasing hormone to stimulate the release of Luteinizing hormone from pituitary cells in culture is demonstrated in FIG. 6. As the concentration of gonadotropin releasing hormone increases from 0 to approximately $10^{-9}$ molar we see a dramatic increase in the amount of LH released from the pituitary cells in culture. The pituitary cell cultures were prepared as described in Example 2. The maximum release of LH is reached by $10^{-7}$ molar gonadotropin releasing hormone. Therefore, this profile illustrates the natural response to pituitary cells to gonadotropin releasing hormone. This control curve is used to evaluate the extent of inhibition due to the presence of an Antagonist.

Example 7

Improved procedure for production of agonist complex

Figure 9:
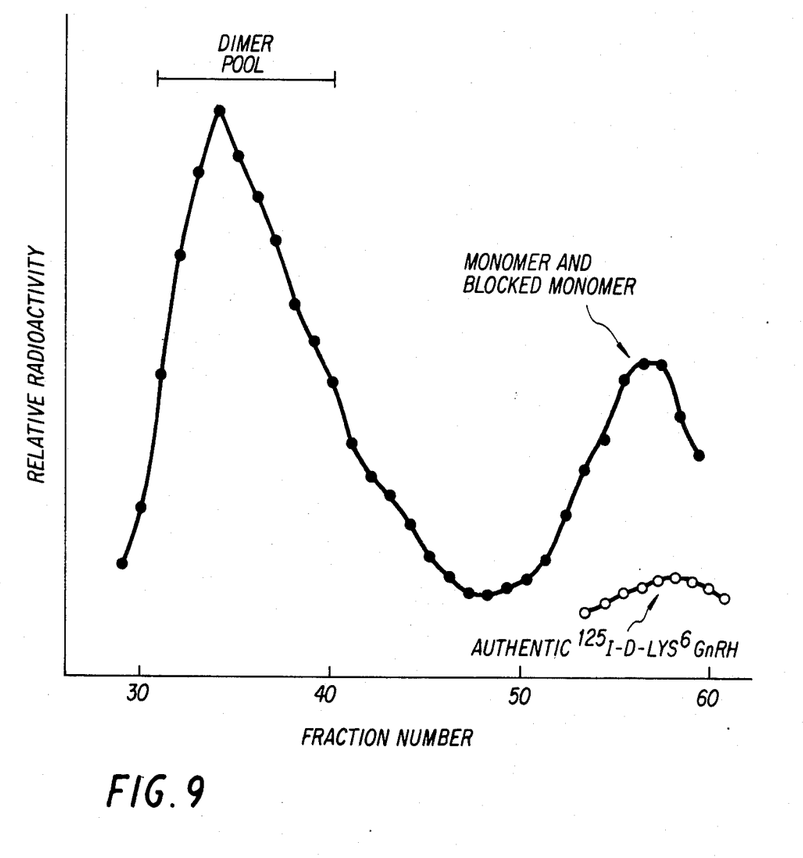
FIG. 9—Elution profile following gel filtration on G-25 Sephadex, Supertive of [$^{125}$I]-tyr$^5$-D-Lys$^6$-GnRH following 7 hour dimerization reaction.

The following is an improved method of producing a synthetic hormone complex similar to that shown in Examples 3 and 4. The principle improvement is an increased efficiency in producing the agonist complex as shown in FIG. 9. Here, there is Dimer formation of 40% of the total D-Lys$^6$-GnRH added to the reaction mixture after a 7 hour dimerization reaction.

Higher order multimers are not seen; this is not surprising since D-Lys$^6$-GnRH has only a single reactive site (the N-terminal is blocked). A second peak is present which corresponds to the elution position of authentic [$^{125}$I]-Tyr$^5$-D-Lys$^6$-GnRH. This peak likely contains both unreacted and blocked D-Lys$^6$-GnRH monomer (i.e., (D-Lys$^6$-GnRH)-EGS) these differ only slightly in molecular weight and would not be resolved in this chromatographic system.

Figure 10:
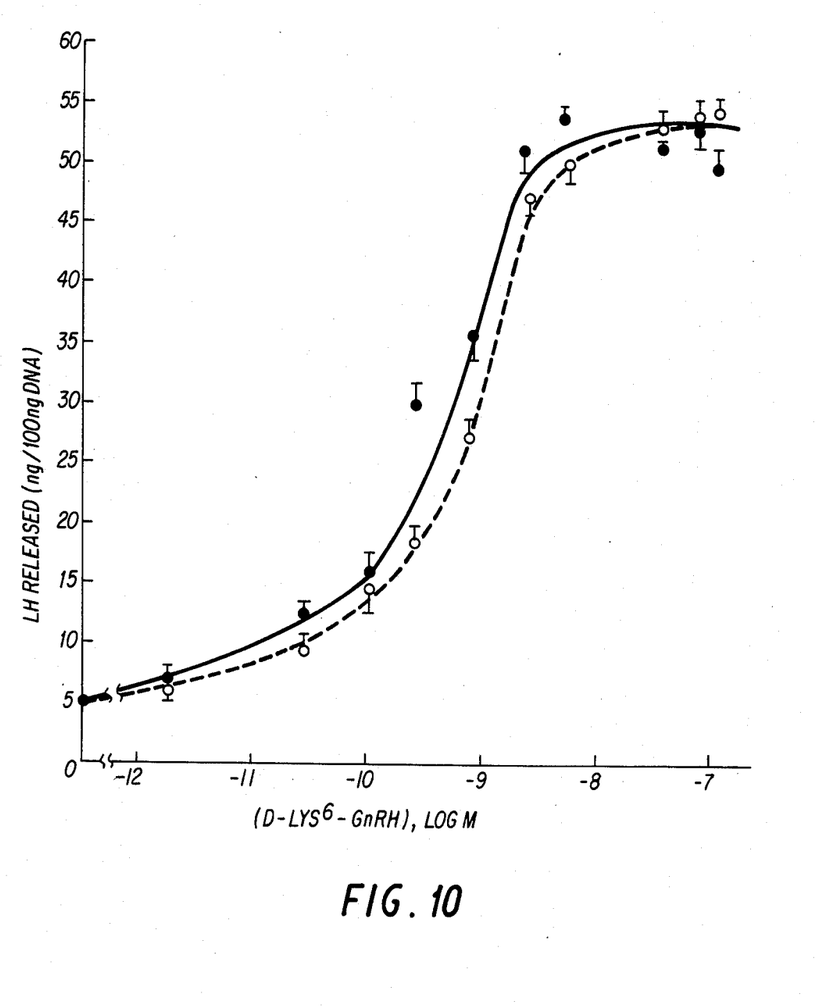
FIG. 10—Luteinizing hormone release in response to the indicated concentration of D-Lys$^6$-GnRH (Solid symbol) or (D-Lys$^6$-GnRH)$_2$-EGS dimer (open symbol).

Luteinizing hormone (LH) release in response to the agonist dimer complex is shown in FIG. 10. LH release has measured as described in Example 4.

The ED$_{50}$ values (Molar in terms of D-Lys$^6$-GnRH) are $5 \times 10^{-10}$M and $8 \times 10^{-10}$M. The ED$_{10}$ value for the dimer was approximately $3 \times 10^{-11}$ in terms of D-Lys$^6$-GnRH concentration or $1.5 \times 10^{-11}$ in terms of dimer.

FIG. 11 shows (solid symbol) the effect of adding the indicated titer of antibody after addition of $1.5 \times 10^{-11}$ dimer followed by antisera. Optimum potentiation is seen at antibody titer 1:10$^5$–1:10$^6$. For comparison, $10^{-7}$M D-Lys$^6$-GnRH stimulated LH release was 58±6 ng/100 ng DNA in this study. The antibody cross-linked dimer thus stimulated response at about the ED$_{40}$ level. Monovalent antibody (reduced pepsin fragments) was ineffective in stimulating release in the presence $1.5 \times 10^{-11}$M dimer (mean release=5.1±0.5 ng/100 ng DNA at all titers). The addition of 5 μM Pimozide or 2 mM EGTA diminished LH release to near basal, at all titers in the presence of $1.5 \times 10^{-11}$M dimer. Addition of antibody alone (open symbol) did not stimulate LH release over basal levels (5.0±0.5 ng/100 ng DNA).

Thus, addition of antibody prepared against D-Lys$^6$-GnRH to (D-Lys$^6$)$_2$EGS dimer enhances the potency of the dimer; that is, the dimer was able to stimulate gonadotropin release at concentrations which, in the absence of antibody was minimally effective. These observations support the view that formation of a microaggregate of the GnRH receptor is sufficient to transduce the signal across the plasma membrane and elicit cell responses if the separation distance between ligands is increased to a critical point. The dimer alone, with only a 150 Å bridge length is unable to do this, while the conjugate (i.e., dimer)$_2$-antibody complex about 150 Å bridge length) is apparently of sufficient length.

Therefore, the best mode approach for producing the agonist dimer complex requires incubation of the reaction mixture for 7 hours or more.

The synthetic hormone complexes can be formulated in dosage forms for oral, nasal, parenteral, or rectal administration. Solid dosage forms for oral administration include capsules, tablets and pills. In such solid dosage forms, the active compound is admixed with at least one inert diluent such as sucrose, lactose, or starch. In the case of capsules, tablets and pills, the dosage forms may be also comprise buffering agents. Tablets and pills can additionally be prepared with an enteric coating.

Liquid dosage forms for oral administration include syrups and elixirs containing inert diluents commonly used in the art, such as purified water. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate.

Compositions for rectal administration are suppositories which may contain in addition to the active substance, excipients such as cocoa butter or a suppository wax.

A preferred method of administering the synthetic hormone complexes in the method of this invention is to inject a composition comprising the complex and a slow release excipient, i.e., an excipient that is not immediately absorbed by the body wherein it slowly releases the synthetic hormone complex contained therein to provide a hightened serum concentration of the complex for an extended prior of time.

Having now fully described the invention, it will be apparent to one of ordinary skill in the art that many changes and modifications may be made without departing from the spirit or the scope of the invention as set forth herein. Applicant does not wish to be bound by any theory of how the synthetic hormone complex functions. Other processes or mechanisms not now known may also be stimulated by the administration of the synthetic hormone complexes which result in beneficial effects due to altering the incorporation of calcium ions by cells.

What is claimed as new and desired to be secured by Letters Patent of the United States is:

1. A synthetic gonadotropin releasing hormone conjugate, which functions as a gonadotropin releasing hormone agonist and consists of
   (a) gonadotropin releasing hormone or a biologically active analog thereof which comprises a D-lysine at the 6 position of gonadotropin releasing hormone to which another said gonadotropin releasing hormone or gonadotropin releasing hormone analog is covalently bound via a covalent spacer, wherein said spacer comprises a C$_1$ to C$_{20}$ hydrocarbon chain and said spacer is from 10–300 Å in length, thereby producing a dimer, and
   (b) wherein said dimer is bound via a gonadotropin releasing hormone antibody to another of said dimer to produce said conjugate having gonadotropin releasing hormone agonistic activity.

2. The conjugate of claim 1, wherein said dimer comprises 2 molecules of gonadotropin releasing hormone.

3. The conjugate of claim 1, wherein said dimer comprises 2 molecules of said analog.

4. A synthetic gonadotropin releasing hormone conjugate, which functions as a gonadotropin releasing hormone antagonist and consists of gonadotropin releasing hormone covalently bound via a covalent spacer, which comprises a C$_1$ to C$_{20}$ hydrocarbon chain, wherein said spacer is from 10–300 Å in length, to a synthetic calcium ion channel inhibitor selected from the group consisting of methoxy-[3-[[2-(3,4-Dimethoxyphenyl)ethyl]-methylamino]propyl]-3,4-dimethoxy-α-(1-methylethyl)benzeneacetonitrile;

5-((3,4-dimethoxyphenethyl)methylamino-2-(3,4-dimethoxyphenyl)-2-isopropylvaleronitrile;

1,4-dihydro-2,6-dimethyl-4-(2-nitrophenyl)-3,5-pyridinedicarboxylic acid dimethyl ester;

1,4-dihydro-2,6-dimethyl-4-(2-isothiocyanatophenyl)-3,5-pyridinedicarboxylic acid dimethyl ester;

1-[bis(4-fluorophenyl)methyl]-4-(3-phenyl-2-propenyl)-piperazine;

1-(diphenylmethyl)-4-(3-phenyl-2-propenyl)-piperazine;

bis(2-propoxyethyl)-1,4-dihydro-2,6-dimethyl-4-(m-nitrophenyl)-3,5-pyridine-dicarboxylate;

N-(1-methyl-2-phenylethyl)-γ-phenylbenzenepropanamine; and cis-(+)-3-(acetyloxy)-5-(2-(dimethylamino)ethyl)-2,3-dihydro-2-(4-methoxyphenyl)-1,5-benzothiazepin-4(5H)-one, wherein said conjugate exhibits gonadotropin releasing hormone antagonistic activity.

5. The conjugate of claim 4, wherein said synthetic calcium ion channel inhibitor is methoxy-[3-[[2-(3,4-Dimethoxyphenyl)ethyl]-methylamino]propyl]-3,4-dimethoxy-α-(1-methylethyl)benzeneacetonitrile.

6. The conjugate of claim 4, wherein said synthetic calcium ion channel inhibitor is 5-((3,4-dimethoxyphenethyl)methylamino-2-(3,4-dimethoxyphenyl)-2-isopropylvaleronitrile.

7. The conjugate of claim 4, wherein said synthetic calcium ion channel inhibitor is 1,4-dihydro-2,6-dimethyl-4-(2-nitrophenyl)-3,5-pyridinedicarboxylic acid dimethyl ester.

8. The conjugate of claim 4, wherein said synthetic calcium ion channel inhibitor is 1,4-dihydro-2,6-dimethyl-4-(2-isothiocyanatophenyl)-3,5-pyridinedicarboxylic acid dimethyl ester.

9. The conjugate of claim 4, wherein said synthetic calcium ion channel inhibitor is 1-[bis(4-fluorophenyl)-methyl]-4-(3-phenyl-2-propenyl)piperazine.

10. The conjugate of claim 4, wherein said synthetic calcium ion channel inhibitor is 1-(diphenylmethyl)-4-(3-phenyl-2-propenyl)-piperazine.

11. The conjugate of claim 4, wherein said synthetic calcium ion channel inhibitor is bis(2-propoxyethyl)-1,4-dihydro-2,6-dimethyl-4-(m-nitrophenyl)-3,5-pyridine-dicarboxylate.

12. The conjugate of claim 4, wherein said synthetic calcium ion channel inhibitor is N-(1-methyl-2-phenylethyl)-γ-phenylbenzenepropanamine.

13. The conjugate of claim 4, wherein said synthetic calcium ion channel inhibitor is cis-(+)-3-(acetyloxy)-5-(2-(dimethylamino)ethyl)-2,3-dihydro-2-(4-methoxyphenyl)-1,5-benzothiazepin-4(5H)-one.

14. A method of stimulating the release of lutinizing hormone in a mammal, which comprises:
administering to said mammal a therapeutically effective amount a synthetic gonadotropin releasing hormone conjugate, which functions as a gonadotropin releasing hormone agonist and consists of
(a) gonadotropin releasing hormone or a biologically active analog thereof which comprises a D-lysine at the 6 position of gonadotropin releasing hormone to which another said gonadotropin releasing hormone or gonadotropin releasing hormone analog is covalently bound via a covalent spacer, wherein said spacer comprises a $C_1$ to $C_{20}$ hydrocarbon chain and said spacer is from 10–300 Å in length, thereby producing a dimer, and
(b) wherein said dimer is bound via a gonadotropin releasing hormone antibody to another of said dimer to produce said conjugate having gonadotropin releasing hormone agonistic activity.

15. The method of claim 14, wherein said dimer comprises 2 molecules of gonadotropin releasing hormone.

16. The method of claim 14, wherein said dimer comprises 2 molecules of said analog.

17. A method of inhibiting the release of lutinizing hormone in a mammal, which comprises:
administering to said mammal a therapeutically affective amount of a synthetic gonadotropin releasing hormone conjugate, which functions as a gonadotropin releasing hormone antagonist and consists of gonadotropin releasing hormone covalently bound via a covalent spacer, which comprises a $C_1$ to $C_{20}$ hydrocarbon chain, wherein said spacer is from 10–300 Å in length, to a synthetic calcium ion channel inhibitor selected from the group consisting of methoxy-[3-[[2-(3,4-Dimethoxyphenyl)ethyl]-methylamino]propyl]-3,4-dimethoxy-α-(1-methylethyl)benzeneacetonitrile;

5-((3,4-dimethoxyphenethyl)methylamino)-2-(3,4-dimethoxyphenyl)-2-isopropylvaleronitrile;

1,4-dihydro-2,6-dimethyl-4-(2-nitrophenyl)-3,5-pyridinedicarboxylic acid dimethyl ester;

1,4-dihydro-2,6-dimethyl-4-(2-isothiocyanatophenyl)-3,5-pyridinedicarboxylic acid dimethyl ester;

1-[bis(4-fluorophenyl)methyl]-4-(3-phenyl-2-propenyl)-piperazine;

1-(diphenylmethyl)-4-(3-phenyl-2-propenyl)-piperazine;

bis(2-propoxyethyl)-1,4-dihydro-2,6-dimethyl-4-(m-nitrophenyl)-3,5-pyridine-dicarboxylate;

N-(1-methyl-2-phenylethyl)-γ-phenylbenzenepropanamine; and cis-(+)-3-(acetyloxy)-5-(2-(dimethylamino)ethyl)-2,3-dihydro-2-(4-methoxyphenyl)-1,5-benzothiazepin-4(5H)-one, wherein said conjugate exhibits gonadotropin releasing hormone antagonistic activity.

18. The method of claim 17, wherein said synthetic calcium ion channel inhibitor is methoxy-[3-[[2-(3,4-Dimethoxyphenyl)ethyl]-methylamino]propyl]-3,4-dimethoxy-α-(1-methylethyl)benzeneacetonitrile.

19. The method of claim 17, wherein said synthetic calcium ion channel inhibitor is 5-((3,4-dimethoxyphenethyl)methylamino-2-(3,4-dimethoxyphenyl)-2-isopropylvaleronitrile.

20. The method of claim 17, wherein said synthetic calcium ion channel inhibitor is 1,4-dihydro-2,6-dimethyl-4-(2-nitrophenyl)-3,5-pyridinedicarboxylic acid dimethyl ester.

21. The method of claim 17, wherein said synthetic calcium ion channel inhibitor is 1,4-dihydro-2,6-dimethyl-4-(2-isothiocyanatophenyl)-3,5-pyridinedicarboxylic acid dimethyl ester.

22. The method of claim 17, wherein said synthetic calcium ion channel inhibitor is 1-[bis(4-fluorophenyl)-methyl]-4-(3-phenyl-2-propenyl)piperazine.

23. The method of claim 17, wherein said synthetic calcium ion channel inhibitor is 1-(diphenylmethyl)-4-(3-phenyl-2-propenyl)-piperazine.

24. The method of claim 17, wherein said synthetic calcium ion channel inhibitor is bis(2-propoxyethyl)-

1,4-dihydro-2,6-dimethyl-4-(m-nitrophenyl)-3,5-pyridine-dicarboxylate.

25. The method of claim 17, wherein said synthetic calcium ion channel inhibitor is N-(1-methyl-2-phenylethyl)-γ-phenylbenzenepropanamine.

26. The method of claim 17, wherein said synthetic calcium ion channel inhibitor is cis-(+)-3-(acetyloxy)-5-(2-(dimethylamino)ethyl-2,3-dihydro-2-(4-methoxyphenyl)-1,5-benzothiazepin-4(5H)-one.

* * * * *